United States Patent [19]

Hagi et al.

[11] Patent Number: 5,182,329
[45] Date of Patent: Jan. 26, 1993

[54] PROCESS FOR PRODUCING CARRIERS FOR IMMUNOASSAY

[75] Inventors: Norio Hagi, Yamato; Takahiro Takeyama, Yokohama, both of Japan

[73] Assignee: Tosoh Corporation, Shinnanyo, Japan

[21] Appl. No.: 668,782

[22] Filed: Mar. 13, 1991

[30] Foreign Application Priority Data

Mar. 13, 1990 [JP] Japan ................................. 2-59906
Apr. 5, 1990 [JP] Japan ................................. 2-89238

[51] Int. Cl.⁵ .............................................. C08F 2/00
[52] U.S. Cl. ....................................... 525/242; 521/31;
525/333.3; 525/333.4; 525/333.5; 525/333.6; 526/333
[58] Field of Search .................. 526/333.2; 525/242, 525/333.3, 333.4, 333.5, 333.6; 521/31

[56] References Cited

U.S. PATENT DOCUMENTS

| | | | |
|---|---|---|---|
| 3,620,368 | 11/1971 | Comis et al. | 528/502 |
| 4,582,792 | 4/1986 | Kasahara et al. | 436/523 |
| 4,622,346 | 11/1986 | DiGiulio | 525/242 |
| 4,626,554 | 12/1986 | DiGiulio | 525/242 |
| 4,996,265 | 2/1991 | Okubo et al. | 525/242 |

FOREIGN PATENT DOCUMENTS 0234083 9/1987 European Pat. Off. .

OTHER PUBLICATIONS

Database Chemical Abstracts, 1986, 57456U, & JP-A-61-016,912, Jan. 24, 1986.
Database Chemical Abstracts, 1987, 109239J, & JP-A-62-200,264, Sep. 3, 1987.
Database Chemical Abstracts, 1982, 50013A, & JP-A-57-168,163, Oct. 16, 1981.

Primary Examiner—Paul R. Michl
Assistant Examiner—Olga Asinovsky
Attorney, Agent, or Firm—Oblon, Spivak, McClelland, Maier & Neustadt

[57] ABSTRACT

A process for producing carriers for immunoassay, which comprises:

① a step of cutting a polystyrene material into pellets,

② a step of polymerizing the polystyrene pellets and a monomer required for forming polystyrene in the presence of a polymerization initiator and a crosslinking agent in a medium in which the pellets and the monomer are hardly soluble, to obtain spherical polystyrene beads, and ③ a step of roughening the surface of the spherical polystyrene beads.

15 Claims, 5 Drawing Sheets

PROCESS FOR PRODUCING CARRIERS FOR IMMUNOASSAY

The present invention relates to a process for producing carriers for immunoassay. More particularly, it relates to a process for producing carriers which are superior to conventional materials in the physical adsorptivity for a substance to be used for immunoassay such as an antibody or an antigen, particularly a protein.

It is generally known that the content of a substance such as a protein contained in a very small amount in a body fluid such as blood serum or urine, can be determined by an immunoassay using an antibody or an antigen.

In a measuring kit for such immunoassay, it is common to employ insoluble carriers for fixing or immobilizing the antibody or the antigen. For this purpose, a plastic material such as polystyrene has been used.

For the production of conventional plastic carriers such as polystyrene carriers, it is common to preliminarily determine the shape and size and prepare a retaining mold, and then conduct molding. Such a method has a problem that for the determination and preparation of the mold, substantial time and costs are required. Yet, from a mold of one type, it is possible to produce a carrier of one type only. Therefore, when it is desired to change the size or shape of the carrier, it is necessary to prepare a mold afresh. Further, there is a problem in the production efficiency, since only one molded product (carrier) is produced from one mold by one operation. Namely, when a large amount of the carrier is required, it is necessary to repeat the production process many times.

In addition to such a problem in the production efficiency, the carrier produced by the conventional technique has a problem such that it has low physical absorptivity for a protein such as an antibody or an antigen to be used for immunoassay and is unable to bind a sufficient amount of an antigen or an antibody required for conducting the assay with high precision.

The present inventors have studied the above mentioned problems of the conventional techniques and have conducted a research for a process which is capable of producing a large amount of spherical carriers of an optional size by a single operation and which is capable of producing carriers having high adsorptivity for proteins such as antibodies or antigens. As a result, the present invention has been accomplished.

The present invention accomplished by the research by the present inventors as described above, is a process for producing carriers for immunoassay, which comprises:

① step of cutting a polystyrene material into pellets,

② a step of polymerizing the polystyrene pellets and a monomer required for forming polystyrene in the presence of a polymerization initiator and a crosslinking agent in a medium in which the pellets and the monomer are hardly soluble, to obtain spherical polystyrene beads, and ③ a step of roughening the surface of the spherical polystyrene beads.

In the accompanying drawings:

FIG. 2 (b) is a photograph of scanning electron microscopy of the same pellet (1,000 magnifications).

FIG. 3 (b) is a photograph of scanning electron microscopy of the same bead (1,000 magnificaitons).

FIG. 4 (b) is a photograph of scanning electron microscopy of the same bead (1,000 magnifications).

FIG. 5 (b) is a photograph of scanning electron microscopy of the same bead (1,000 magnifications).

Figure 1:
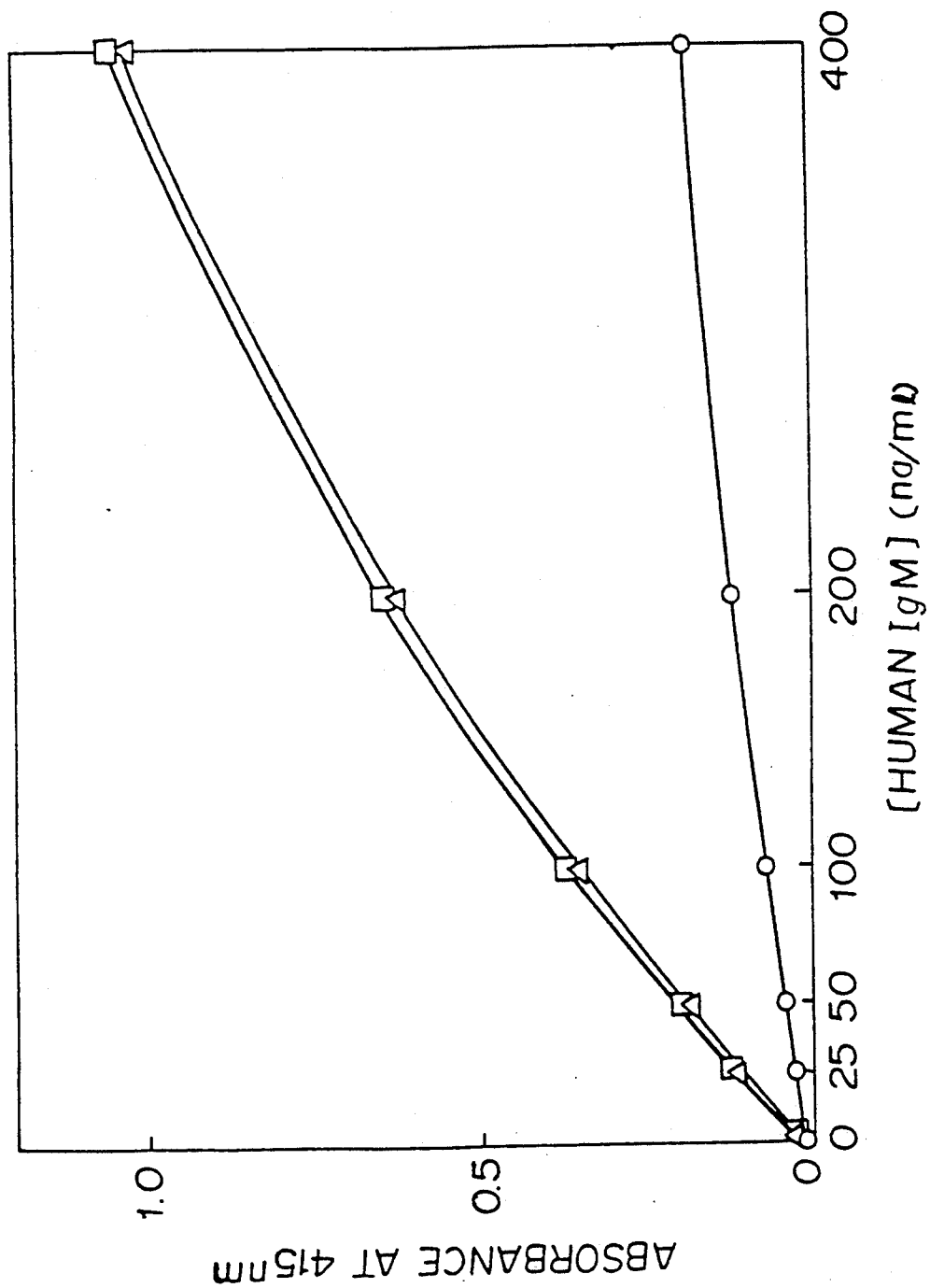
FIG. 1 is a graph showing the results of the immunoassay conducted in Example 7.

Now, the present invention will be described in detail.

The process for producing carriers for immunoassay presented by the present invention is a process for producing spherical carriers having optional sizes and high physical adsorptivity for proteins such as antigens or antibodies in a large amount by a single operation. In the present invention, "spherical carriers" does not necessarily mean exactly spherical carriers but means substantially spherical carriers.

The polystyrene material to be used in step ① in the present invention may not necessarily be a material composed solely of polystyrene, and there is no particular restriction so long as it is a plastic material containing at least about 50% of polystyrene. Here, it is known to use carriers for immunoassay containing a magnetic substance such as ferrite or cobalt to facilitate an operation such as stirring of reactive components during the assay or separation of the carriers from the aqueous phase. When such carriers are to be produced, the polystyrene material may contain an optional amount of a magnetic material.

If it is unnecessary to produce carriers having a uniform size, the pellets in this step may be those obtained by cutting the polystyrene material into suitable sizes. When it is intended to produce carriers having a uniform size, the pellets mean pellets of the polystyrene material cut to have a substantially uniform weight. Such pellets cut to have a uniform weight can readily be obtained, for example, by extrusion of the polystyrene material.

In the process of the present invention, there is no particular restriction as to the size (weight) of pellets to be used. However, taking the efficiency in carrying out the following steps into consideration, it is advisable to employ a size of from about 0.2 to 200 mg, particularly from 1 to 3 mg, which is commonly employed for immunoassay.

Then, the pellets obtained in Step ① and a monomer required for forming polystyrene are polymerized in the presence of a polymerization initiator and a crosslinking agent in a medium in which the pellets and the monomer are hardly soluble. The monomer required for forming polystyrene, the polymerization initiator and the crosslinking agent are not particularly limited, and may, for example, be styrene, benzoyl peroxide and divinyl benzene, respectively. As the medium in which the pellets and the monomer are hardly soluble, to be used in this step, a polyvinyl alcohol solution may, for example, be mentioned.

The conditions for carrying out this step vary depending upon various conditions such as the solvent and the weight of the pellets to be used. In a case where the pellets of the above mentioned preferred weight is to be treated together with styrene, divinyl benzene and benzoyl peroxide in water, the polymerization is usually conducted under a temperature condition of from 50° to 100° C. for from 15 minutes to 48 hours, preferably from 1 to 4 hours. In such a case, it is preferred to stir the medium.

By the above step, it is possible to obtain spherical polystyrene beads. However, when other plastic or magnetic material is also used as a polystyrene material, it is possible to obtain spherical polystyrene beads containing such a plastic or magnetic material.

Finally, the surface of the spherical polystyrene beads thus obtained is roughened. This step can be accomplished, for example, by an operation of stirring the spherical polystyrene beads together with a material required for roughening the surface. Specifically, the spherical polystyrene beads may be stirred together with a substance such as aluminum oxide in a medium such as water or methanol in which the polystyrene and the substance used for roughening the surface are insoluble. This step may be conducted at a temperature at which the polystyrene carriers will not deform. Specifically, the temperature may be from 0° to 40° C. The treating time may be at any level so long as the surface of the carriers is sufficiently roughened and is usually above 3 hours. In the case where aluminum oxide is used, the treating time is usually from 15 minutes to 24 hours. Further, this treatment is preferably combined with stirring operation.

In another preferred embodiment, the above described polymerization step is conducted in the presence of an additive inert to the polymerization reaction so that such an additive will be included in the surface of the resulting spherical polystyrene beads. As the additive inert to the polymerization reaction, isoamyl alcohol or toluene may, for example, be used. The surface of the spherical polystyrene beads thus obtained is then treated with an extracting agent or subjected to evaporation treatment in the final surface roughening step. This step is a step of extracting or evaporating the additive inert to polymerization reaction, which was taken into the spherical polystyrene beads in the preceding step. In this step, ethanol or methanol may, for example, be used as the extracting agent. However, the extracting agent is not limited to such specific examples, and may be any agent so long as it is capable of extracting the additive used in the preceding step. On the other hand, the evaporation treatment may be conducted by subjecting the spherical polystyrene beads to reduced pressure treatment or high temperature treatment. In a case where the high temperature treatment is conducted, the temperature may preferably be set within a range of from 40° to 100° C. where the spherical polystyrene beads would undergo no deformation.

According to the present invention, uniform carriers can be produced in a large amount by a single operation of the process. Besides, by the surface roughening, it is possible to produce carriers having higher physical adsorptivity for proteins such as antibodies or antigens, as compared with conventional carriers. Further, in the case of the carriers produced by extraction or evaporation of the additive from the surface of the polystyrene beads, such carriers have pores formed on their surface by the extraction or evaporation of the additive, whereby they have a wider surface area and hence higher physical adsorptivity than usual spherical polystyrene beads.

According to the process of the present invention as described above, it is possible to control the size of final carriers by predetermining the weight of pellets to be used, and it is possible to produce carriers of optional sizes, as the case requires. Further, since a larger amount of proteins can be adsorbed, it is possible to conduct immunoassays with higher precision to obtain analytical results with higher detecting limits, by using the carriers produced by the present invention.

Now, the present invention will be described in further detail with reference to Examples. However, it should be understood that the present invention is by no means restricted to such specific Examples.

EXAMPLE 1

40 g of polyvinyl alcohol (manufactured by Wako Junyaku Kogyo K.K.) was dissolved in 2 l of deionized water, and the solution was heated to 80° C. To this solution, 600 g of polystyrene pellets obtained by cutting into from 1.5 to 1.7 mg a polystyrene (manufactured by Asahi Chemical Industry Co., Ltd.) mixture having 3% by weight of ferrite (manufactured by TOSOH CORPORATION) kneaded thereinto, were added, followed by treatment for one hour under stirring.

Then, a mixture solution obtained by dissolving 2.5 g of benzoyl peroxide (manufactured by Wako Junyaku Kogyo K.K.) in a mixture comprising 225 g of styrene monomer (manufactured by Wako Junyaku Kogyo K.K.) and 25 g of divinyl benzene (manufactured by Tokyo Kasei Kogyo K.K.), was added thereto, followed by treatment for 3 hours under stirring.

By the above steps, spherical polystyrene carriers were obtained.

EXAMPLE 2

500 g of the spherical polystyrene carriers obtained in Example 1, were added together with 50 g of aluminum oxide (manufactured by Nakaraitesuku K.K.) to 500 ml of deionized water, followed by treatment at 25° C. for 24 hours under stirring.

By the above operation, carriers of the present invention having the surface roughened were produced. The obtained carriers were washed with deionized water and then used in Example 3.

EXAMPLE 3

Using 500 spherical polystyrene carriers obtained in Example 2, the following immunoassay was conducted. Further, in order to demonstrate the superiority of the carriers of the present invention in the adsorptivity for a protein, a similar operation was conducted by 500 carriers obtained in Example 1.

Firstly, in accordance with a known method, mouse monoclonal antibodies capable of specifically recognizing human ferritin were obtained, and 0.25 mg of such antibodies were contacted with 500 carriers and left to stand for 24 hours to let them adsorbed on the carriers. After this operation, the carriers were contacted with 1% by weight of bovine serum albumin (BSA) for blocking treatment.

20 μl of a test solution containing human ferritin at a concentration 0 or 472 ng/ml was contacted with 10 carriers out of the carriers treated as described above. Then, 100 μl of mouse monoclonal antibodies capable of recognizing human ferritin at portions different from the above mentioned monoclonal antibodies and labelled with alkaline phosphatase, were added thereto, and the mixture was left to stand at 37° C. for 40 minutes.

The carriers were washed with washing solution (phosphate buffered saline with 0.05% Tween-20 (pH 7.4)). Then, a substrate solution of pH 10 containing 4-methylumbelliferone phosphate (4 MUP) as a substrate for the alkaline phosphatase, was added thereto. Ten minutes later, an enzymatic reaction-terminating solution was added to terminate the reaction, and then the intensity of fluorescence at 450 nm was measured at an excitation wavelength of 360 nm. The results are shown in Table 1.

TABLE 1

|  | 0 ng/ml | 472 ng/ml |
|---|---|---|
| Surface-roughened carriers | 0.90 | 286.91 |
| Surface non-treated carriers | 0.02 | 5.59 |

The numerical value in Table 1 indicates the intensity of fluorescence at 450 nm, and the larger the numerical value, the larger the amount of the decomposed substrate (4-MU). Such a value has an optional unit.

The above results indicate that the spherical polystyrene carriers produced by the process of the present invention and having the surface roughened show a larger intensity of fluorescence than the carriers having the surface not-roughened. Taking the principle of the conducted immunoassay (sandwich measurement) into consideration, it is indicated that the spherical polystyrene carriers produced by the process of the present invention and having the surface roughened, have a larger amount of antibodies on their surface than the carriers having their surface not-roughened.

EXAMPLE 4

10 g of polyvinyl alcohol (manufactured by Wako Junyaku Kogyo K.K.) was dissolved in 500 ml of deionized water, and the solution was heated to 80° C. To this solution, 600 g of polystyrene pellets obtained by cutting into from 1.5 to 1.7 mg a polystyrene (manufactured by Asahi Chemical Industry Co., Ltd.) mixture having 3% by weight of ferrite (manufactured by TOSOH CORPORATION) kneaded thereinto, were added, followed by treatment for one hour under stirring.

Then, a mixture solution obtained by dissolving 2 g of benzoyl peroxide (manufactured by Wako Junyaku Kogyo K.K.) in a mixture comprising 35 g of styrene monomer (manufactured by Wako Junyaku Kogyo K.K.), 15 g of divinyl benzene (manufactured by Tokyo Kasei Kogyo K.K.) and 50 g of isoamyl alcohol (manufactured by Wako Junyaku Kogyo K.K.), was added thereto, followed by treatment at 80° C. for 3 hours under stirring.

By the above steps, spherical polystyrene carriers were obtained.

EXAMPLE 5

The spherical polystyrene carriers obtained in Example 4 were transferred to a round bottom flask and kept at 80° C. under reduced pressure for 2 hours to evaporate isoamyl alcohol.

EXAMPLE 6

Using 500 spherical polystyrene carriers obtained in Example 5, the following immunoassay was conducted. Further, in order to demonstrate the superiority of the carriers of the present invention in the adsorptivity for a protein, a similar operation was conducted by 500 carriers obtained in Example 4.

Firstly, in accordance with a known method, mouse monoclonal antibodies capable of specifically recognizing human ferritin were obtained, and 0.25 mg of such antibodies were contacted with 500 carriers and left to stand for 24 hours to let them adsorbed on the carriers. After this operation, the carriers were contacted with 1% by weight of bovine serum albumin (BSA) for blocking treatment.

20 μl of a test solution containing human ferritin at a concentration 0 or 472 ng/ml was contacted with 10 carriers out of the carriers treated as described above. Then, 100 μl of mouse monoclonal antibodies capable of recognizing human ferritin at portions different from the above mentioned monoclonal antibodies and labelled with alkaline phosphatase, were added thereto, and the mixture was left to stand at 37° C. for 40 minutes.

The carriers were washed with washing solution. Then, a substrate solution of pH 10 containing 4-methylumbelliferone phosphate (4 MUP) as a substrate for the alkaline phosphatase, was added thereto. Ten minutes later, an enzymatic reaction-terminating solution was added to terminate the reaction, and then the intensity of fluorescence at 450 nm was measured at an excitation wave length of 360 nm. The results are shown in Table 2.

TABLE 2

|  | 0 ng/ml | 472 ng/ml |
|---|---|---|
| Carriers after the evaporation treatment | 1.33 | 258.38 |
| Non-treated carriers | 0.02 | 5.59 |

The numerical value in Table 2 indicates the intensity of fluorescence at 450 nm, and the larger the numerical value, the larger the amount of the decomposed substrate (4-MU). Such a value has an optional unit.

The above results indicate that the spherical polystyrene carriers produced by the process of the present invention and subjected to evaporation treatment show a larger intensity of fluorescence than the carriers not subjected to evaporation treatment. Taking the principle of the conducted immunoassay (sandwich measurement) into consideration, it is indicated that the spherical polystyrene carriers produced by the process of the present invention and subjected to evaporation treatment, has a larger amount of antibodies on their surface than the carriers not subjected to evaporation treatment.

EXAMPLE 7

Enzymatic Immunoassay of Human Immunoglobulin M

Using 500 polystyrene carriers obtained in Example 2 or 5, the following immunoassay was conducted. Further, in order to demonstrate the superiority of the carriers of the present invention, a similar assay was conducted using 500 non-treated carriers.

Firstly, 0.5 mg of anti-human IgM antibody (manufactured by BIOSYSTEM COMPANY) was contacted with 500 carriers and left to stand for 24 hours to let it adsorbed on the carriers. After this operation, the carriers were contacted with 1% by weight of bovine serum albumin for blocking treatment.

50 μl of a test solution containing human IgM at a concentration of 0, 25, 50, 100, 200 or 400 ng/ml was contacted with 10 carriers out of the carriers treated as described above. Then, 10 μl of anti-human IgM antibody labelled with horseradish peroxidase (manufactured by TAGO COMPANY), was added thereto, and the mixture was left to stand at 37° C. for one hour. The reaction solution was washed with a washing solution and then treated with a buffer solution of pH 4 containing hydrogen peroxide and ABTS (2-2-azino-di-[3-ethylbenz thiazoline sulfonic acid diammonium salt], manufactured by (BOEHRINGER MANNHEIM COMPANY) as a substrate for peroxidase, at 37° C. for one hour. Then, 100 μl of an aqueous oxalic acid solution was added to terminate the enzymatic reaction, and the absorbance was measured. The results are shown in FIG. 1.

It is evident from the results that as compared with non-treated merely spherical polystyrene carriers, the polystyrene carriers subjected to aluminum oxide treatment or isoamyl alcohol treatment exhibit remarkably improved absorbance and thus are useful for immunoassay.

Figure 2A:
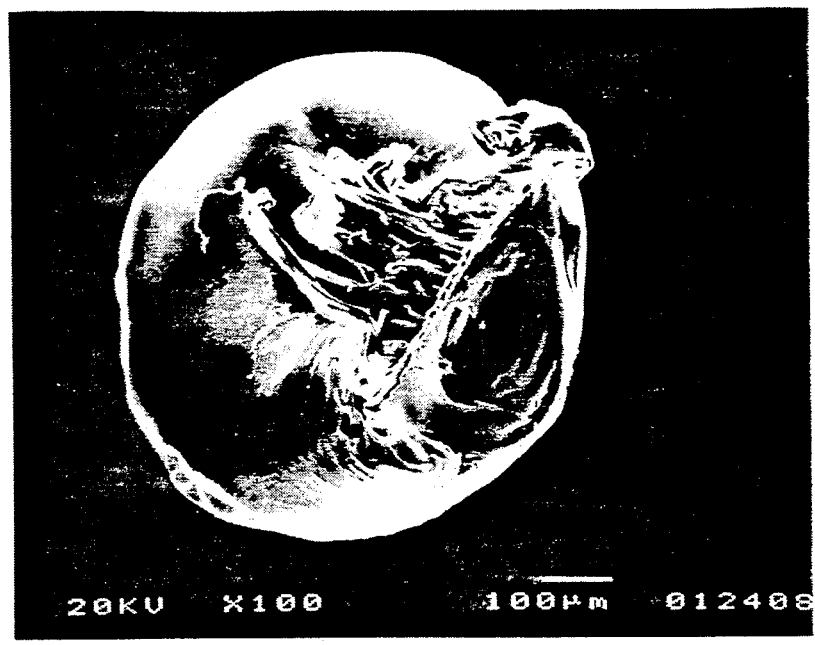
FIG. 2 (a) is an electron microscopic photograph of a polystyrene pellet used as the starting material in Example 1 and 4 (100 magnifications).
Figure 2B:
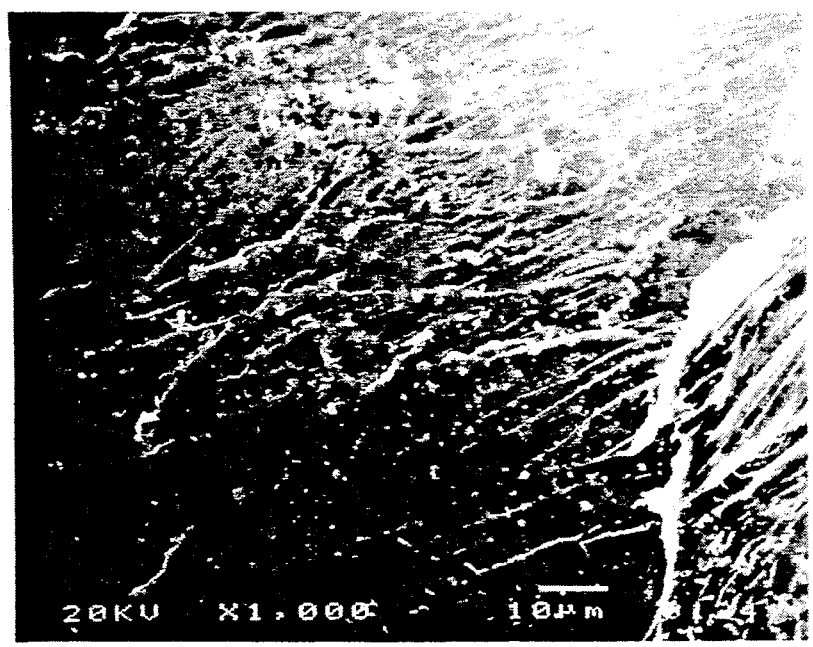
Figure 3A:
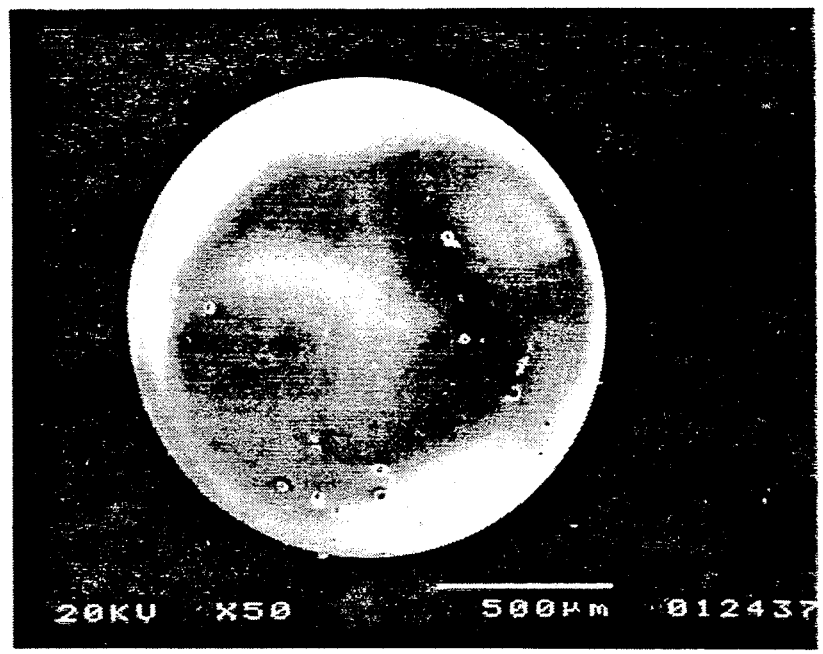
FIG. 3 (a) is an electron microscopic photograph of a polystyrene bead obtained in Example 1 (50 magnifications).
Figure 3B:
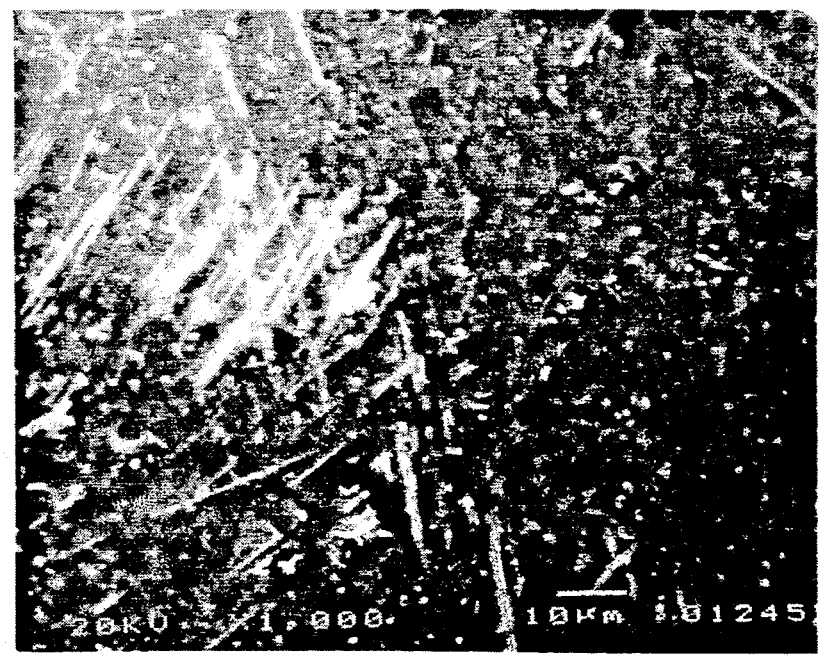
Figure 4A:
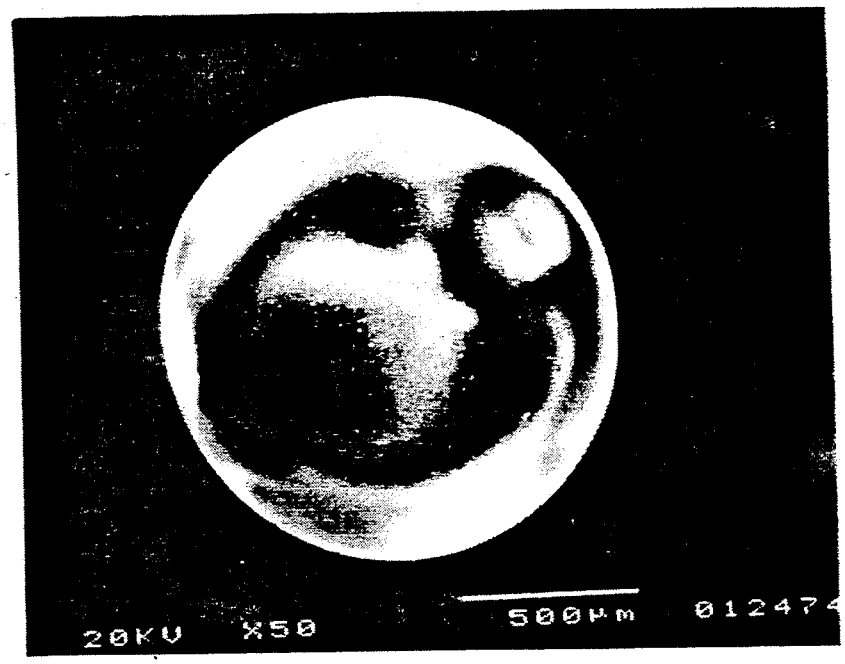
FIG. 4 (a) is an electron microscopic photograph of a polystyrene bead as the carrier of the present invention obtained in Example 2 (50 magnifications).
Figure 4B:
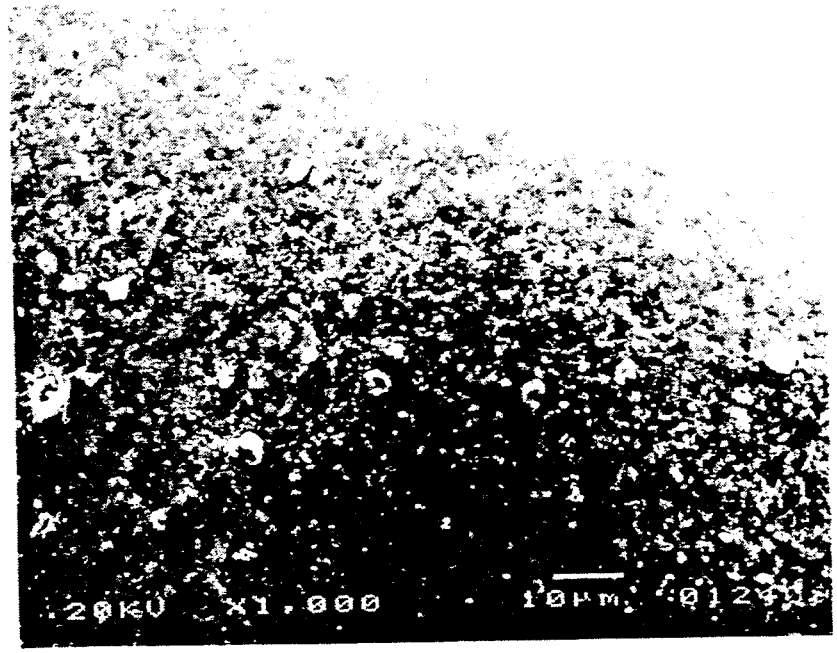
Figure 5A:
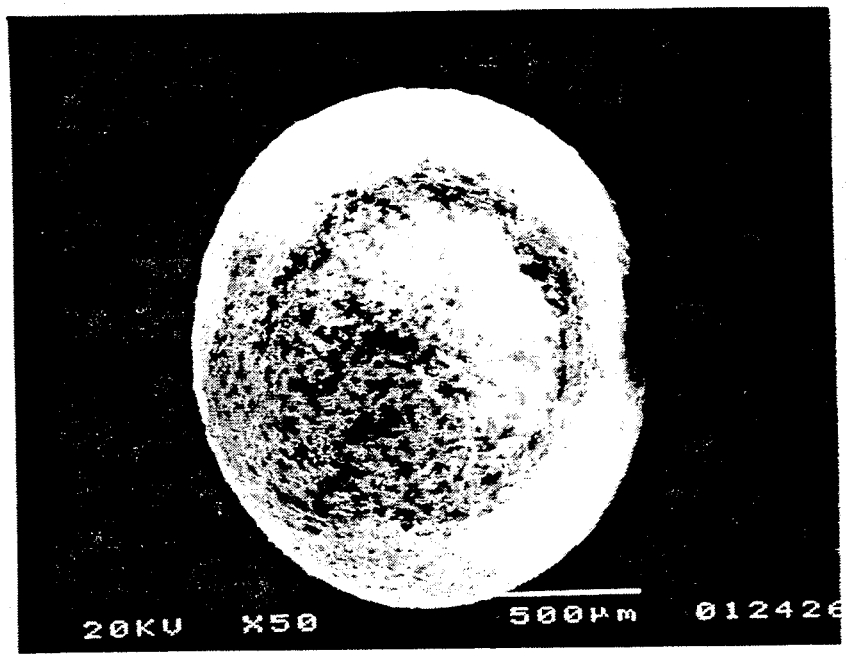
FIG. 5 (a) is an electron microscopic photograph of a polystyrene bead as the carrier of the present invention obtained in Example 5 (50 magnifications).
Figure 5B:
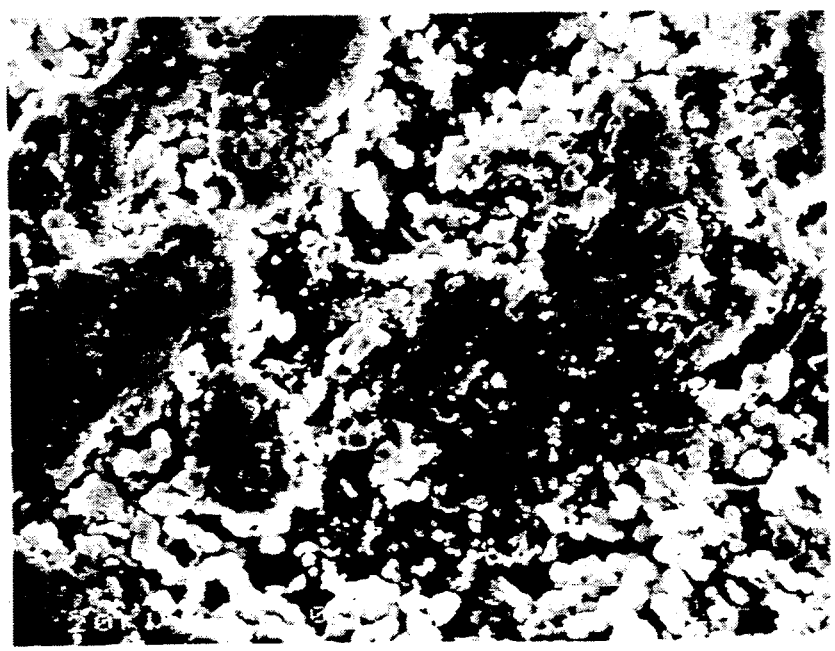

Further, the polystyrene carriers obtained by the present invention and the polystyrene pellets used for the production were photographed by scanning electron microscopy to obtain the photographs as shown in FIGS. 2 (a) to 5 (b). From these Figures, it is evident that pellets of irregular shapes used as the starting material will turn to be spherical according to the present invention. Further, it is evident that the surface layer of the carriers will be roughened by the aluminum oxide treatment or the isoamyl treatment according to the present inveniton. This indicates that the surface area is thereby increased, and thus, such carriers are useful for immunoassay.

We claim:

1. A process for producing carriers for an immunoassay, comprising the steps of:
   ① cutting a polystyrene material into pellets,
   ② polymerizing the polystyrene pellets and a monomer required for forming polystyrene in the presence of a polymerization initiator and a crosslinking agent in a medium in which the pellets and the monomer are hardly soluble, to obtain spherical polystyrene beads, and
   ③ roughening the surface of the spherical polystyrene beads.

2. The process according to claim 1, wherein the monomer required for forming polystyrene is styrene.

3. The process according to claim 1, wherein the polymerization initiator is benzoyl peroxide.

4. The process according to claim 1, wherein the crosslinking agent is divinyl benzene.

5. The process according to claim 1, wherein the medium in which the pellets and the monomer are hardly soluble is water.

6. The process according to claim 1, wherein the polymerization step is conducted by treating the polystyrene pellets together with styrene, divinyl benzene and benzoyl peroxide in water at a temperature of from 50° to 100° C. for from 15 minutes to 48 hours.

7. A process for producing carriers for an immunoassay, comprising the steps of:
   1) cutting a polystyrene material into pellets,
   2) polymerizing the polystyrene pellets and a monomer required for forming polystyrene in the presence of a polymerization initiator and a crosslinking agent in a medium in which the pellets and the monomer are hardly soluble, to obtain spherical polystyrene beads, and
   3) roughening the surface of the spherical polystyrene beads by stirring the spherical polystyrene beads together with aluminum oxide in a medium in which the polystyrene beads and the aluminum oxide are insoluble.

8. A process for producing carriers for an immunoassay, comprising the steps of:
   1) cutting a polystyrene material into pellets,
   2) polymerizing the polystyrene pellets and a monomer required for forming polystyrene in the presence of a polymerization initiator and a crosslinking agent in a medium in which the pellets and the monomer are hardly soluble, to obtain spherical polystyrene beads, and
   3) roughening the surface of the spherical polystyrene beads, wherein the polymerization step is conducted in the presence of an additive inert to the polymerization reaction to obtain spherical polystyrene beads having the additive contained in their surface, and the surface roughening step is conducted by treating the surface of the spherical polystyrene beads with an extracting medium or subjecting the surface to evaporation treatment.

9. The process according to claim 8, wherein the additive inert to the polymerization reaction is isoamyl alcohol or toluene.

10. The process according to claim 8, wherein ethanol or methanol is used as the extracting medium.

11. The process according to claim 8, wherein the evaporation treatment is conducted by subjecting the spherical polystyrene beads to reduced pressure treatment or high temperature treatment at a temperature of from 40° to 100° C.

12. A process for producing carriers for an immunoassay, comprising the steps of:
   1) cutting a polystyrene material into pellets,
   2) polymerizing the polystyrene pellets and a monomer required for forming polystyrene in the presence of a polymerization initiator and a crosslinking agent in a polyvinyl alcohol solution, to obtain spherical polystyrene beads, and
   3) roughening the surface of the spherical polystyrene beads.

13. The process according to claim 12, comprising polymerizing the polystyrene pellets together with styrene, divinyl benzene and benzoyl peroxide.

14. The process of claim 7, comprising polymerizing the polystyrene pellets together with styrene, divinyl benzene and benzoyl peroxide in water or a polyvinyl alcohol solution.

15. The process of claim 8, comprising polymerizing the polystyrene pellets together with styrene, divinyl benzene and benzoyl peroxide in water or a polyvinyl alcohol solution.

* * * * *